United States Patent [19]

Emi et al.

[11] Patent Number: 4,463,095
[45] Date of Patent: Jul. 31, 1984

[54] PROCESS FOR PRODUCING α-GLYCEROPHOSPHATE OXIDASE

[75] Inventors: Shigenori Emi; Yoshio Kojima, both of Tsuruga; Makoto Ando, Ootsu, all of Japan

[73] Assignee: Toyo Boseki Kabushiki Kaisha, Osaka, Japan

[21] Appl. No.: 444,374

[22] Filed: Nov. 26, 1982

[51] Int. Cl.³ .......................... C12N 9/04; C12R 1/01; C12R 1/225; C12R 1/46
[52] U.S. Cl. .................................. 435/190; 435/822; 435/853; 435/885
[58] Field of Search ......................................... 435/190

[56] References Cited

U.S. PATENT DOCUMENTS 4,322,496 3/1982 Esders .................................... 435/25

Primary Examiner—Lionel M. Shapiro
Attorney, Agent, or Firm—Wenderoth, Lind & Ponack

[57] ABSTRACT

α-glycerophosphate oxidase is produced by cultivating microorganisms belonging to genus Pediococcus, Streptococcus, Lactobacillus or Leuconostoc in a nutrient medium containing at least one compound selected from the group consisting of α-keto acids represented by the formula,

R—COCOOH wherein R is $CH_3(CH_2)_m-$, $HOOC(CH_2)_n-$ or $CH_2(OH)CH(OH)CH(OH)CH-$ (in which m is an integer of 1 to 3 and n is an integer of 0 to 2) and salts thereof, and then α-glycerophosphate oxidase is recovered from the resulting culture broth. α-ketobutyric acid, α-ketovaleric acid, α-ketocaproic acid, α-ketomalonic acid, oxalacetic acid, α-ketoglutaric acid and α-ketogluconic acid are disclosed.

6 Claims, No Drawings

PROCESS FOR PRODUCING α-GLYCEROPHOSPHATE OXIDASE

The present invention relates to a method for producing α-glycerophosphate oxidase in good efficiency.

It is so far well known that α-glycerophosphate oxidase (hereinafter referred to as α-GPO) is produced by microorganisms belonging to genus Streptococcus (Archives of Biochemistry and Biophysics, Vol. 88, 250, 1960), microorganisms belonging to genus Lactobacillus (Journal of Biological Chemistry, Vol. 234, 2794, 1959), *Leuconostoc mesenteroides, Pediococcus cerevisiae* (Japanese Patent Application Kokai No. 72892/1978) and microorganisms belonging to genus Aerococcus (Japanese Patent Application Kokai No. 15746/1980).

α-GPO is known to be capable of being used for the quantitative analysis of L-α-glycerophosphate in serum or other samples, that of glycerol by combination with glycerol kinase, and that of triglyceride by coupled reaction with lipoprotein lipase and glycerol kinase, and therefore α-GPO is attracting attention as a reagent for research and clinical diagnosis.

In order to respond to such demand, the present inventors extensively studied a method for producing α-GPO industrially and cheaply, and as a result, found that the producibility of α-GPO is markedly increased by cultivating an α-GPO producing microorganism belonging to genus Pediococcus, Streptococcus, Lactobacillus or Leuconostoc in a nutrient medium containing at least one compound selected from the group consisting of oxalacetic acid, α-ketobutyric acid, α-ketovaleric acid, α-ketogluconic acid, α-ketoglutaric acid and salts thereof.

According to the present invention, there is provided a method for producing α-glycerophosphate oxidase characterized in that an α-glycerophosphate oxidase producing microorganism belonging to genus Pediococcus, Streptococcus, Lactobacillus or Leuconostoc is cultivated in a nutrient medium containing at least one compound selected from the group consisting of α-keto acids represented by the formula,

R—COCOOH wherein R is $CH_3(CH_2)_m$—, $HOOC(CH_2)_n$— or $CH_2(OH)CH(OH)$—$CH(OH)CH$— (in which m is an integer of 1 to 3 and n is an integer of 0 to 2), and salts thereof, and then the objective α-glycerophosphate oxidase is recovered from the resulting culture broth.

Thus, the present invention provides a method for producing α-glycerophosphate oxidase characterized in that the α-GPO producing microorganism is cultivated in a nutrient medium to which a member of the foregoing α-keto acids and salts thereof has been added, and the objective α-glycerophosphate oxidase is recovered from the resulting culture broth.

According to the present invention, by adding ascorbic acid, α-ketoglutaric acid or its salt to a nutrient medium, the producibility of α-GPO can be markedly increased as compared with those cases where such acid or salt is not added.

As the strain to be used in the present invention, there may be mentioned for example α-glycerophosphate oxidase producing microorganisms belonging to genus Pediococcus such as *Pediococcus acidilactici, Pediococcus cerevisiae, Pediococcus homari, Pediococcus parvulus, Pediococcus pentosaceus, Pediococcus urinae-equi* and the like. Further, α-glycerophosphate oxidase producing microorganisms belonging to genus Streptococcus such as *Streptococcus faecalis, Streptococcus salvarius, Streptococcus cremoris, Streptococcus faecium*, etc., those belonging to genus Lactobacillus such as *Lactobacillus planterum, Lactobacillus delbrueckii, Lactobacillus fermentum, Lactobacillus pentoaceticus, Lactobacillus lactis, Lactobacillus buchneri, Lactobacillus leichmannii*, etc., and those belong to genus Leuconostoc such as *Leuconostoc mesenteroides*, etc. may also be used.

More particular examples of strains useful in the present invention include *Pediococcus acidilactici* (FERM BP-211), *Pediococcus cerevisiae (FERM BP-*213), *Pediococcus pentosaceus* (FERM BP-215), *Pediococcus parvulus* (FERM BP-214), *Pediococcus homari* (FERM BP-212), *Pediococcus urinae-equi* (ATCC 29722), *Streptococcus faecalis* (IFO 3971), *Streptococcus faecium* (ATCC 14432), *Lactobacillus leichmannii* (ATCC 4797), *Lactobacillus fermentum* (ATCC 9338), etc. which are known per se and readily and publicly available from the respective depositories, e.g. FERM or FRI (Fermentation Research Institute, Ibaragi, Japan) and ATCC.

In cultivating the above microorganisms in a culture medium, the method of the present invention is characterized in that at least one compound selected from the group consisting of α-keto acids represented by the aforementioned formula (e.g. α-ketobutyric acid, α-ketovaleric acid, α-ketocaproic acid, α-ketomalonic acid, oxalacetic acid, α-ketoglutaric acid, α-ketogluconic acid) and the salts thereof is added to the culture medium to increase the productivity of the objective enzyme.

As the salt of these acids, there may be mentioned alkali metal salts such as sodium salt, potassium salt, etc., and alkaline earth metal salts such as calcium salt, etc.

The culture medium to be used in the present invention may be any of those commonly used for the cultivation of this species of microorganisms except that the particular acid or salt as defined above is added to the medium. Such culture medium usually contains proper carbon source, nitrogen source, inorganic salt and organic growth factor. As the carbon source, glycerol, glucose, fructose, lactose, sucrose, blackstrap molasses or the like may be used. As the nitrogen source, organic nitrogen sources such as peptone, yeast extract, meat extract, corn steep liquor and the like are preferred. As the inorganic salt, salts of metals such as potassium, sodium, manganese, magnesium, zinc, iron, etc., and salts of sulfuric acid, phosphoric acid, hydrochloric acid, nitric acid, etc. may be used. As the organic growth factor, yeast extract and corn steep liquor are particularly useful.

The amount of ascorbic acid, the α-keto acids or the salts thereof used in the present invention is 1 g to 10 g, preferably 2 g to 5 g per liter of culture medium. Preferably the pH of the culture medium is kept about neutral, and aerobic cultivation such as aeration-agitation is carried out at 25° to 32° C. for 10 to 30 hours to accumulate α-GPO in the cell.

For extracting and recovering α-GPO from the cell thus obtained, the cell is treated by either of the well-known methods such as mechanical grinding, ultrasonic treatment, autolysis, lysozyme treatment and the like, or by the proper combination of these methods to obtain a cell-free enzyme solution, and then the resulting solution is treated by the well-known methods such as salting-out with ammonium sulfate, precipitation with a solvent such as acetone, alcohol or the like to obtain an enzyme preparation. For obtaining more highly purified enzyme preparations, it is recommended by employ ion-exchange chromatography or molecular sieves.

The determination of the enzymatic activity of α-GPO obtained according to the present invention and the properties thereof will be illustrated with reference to a typical example which is a α-GPO of *Pediococcus pentosaceus* (FERM BP-215) (purified enzyme of 34.2 unit/mg obtained in Example 2 described later).

A. Determination of enzymatic activity

Enzymatic activity can be obtained by causing α-GPO to act on D,L-α-glycerophosphate and determining the formed hydrogen peroxide. That is, the enzymatic activity of α-GPO is obtained by decomposing the formed hydrogen peroxide with peroxidase (POD) in the presence of o-aminophenol whereby the o-aminophenol is quantitatively oxidized at the same time and colorimetrically determining the developed coloring compound at 480 nm. The composition of the enzymatic reaction solution and the reaction condition are as follows:

(1) Composition of reaction solution:
0.45M aqueous D,L-α-glycerophosphate solution (pH 7.0): 1.0 ml
0.45M K-phosphate buffer solution (pH 7.0) (containing 0.125% (W/V) of Triton X-100): 1.0 ml
Aqueous POD solution (15 purpurogallin units/ml): 1.0 ml
0.001M aqueous o-aminophenol hydrochloride solution: 1.0 ml
Enzyme solution (0.004–0.015 unit/ml): 0.5 ml (2) Reaction condition:
The reaction is carried out at 37° C. for 10 minutes, and then terminated with addition of 0.5 ml of 4N hydrochloric acid. The formed coloring compound is colorimetrically determined at 480 nm.

(3) Enzymatic activity:
One unit of the enzyme is defined by the amount of the enzyme which produces 1 μmole of hydrogen peroxide in one minute under the aforementioned reaction condition.

B. Action

The present enzyme uniquely oxidizes L-α-glycerophosphate to catalyze the reaction producing dihydroxyacetone phosphate and hydrogen peroxide.

C. Enzymatic properties (1) Optimum pH and pH stability:
The optimum pH of the present enzyme was examined with a Tris-hydrochloric acid buffer solution (pH 7.0–9.5) and $K_2CO_3$-$NaHCO_3$ buffer solution (pH 9.0–10.5) to find that it is 8.0 to 8.5. The pH region in which the present enzyme is kept stable is in a range of 6.5 to 8.5 at a 25° C.×20 hours treatment (ph 5.0–7.0, 0.1M dimethylglutaric acid-NaOH buffer solution; pH 7.0–8.8, 0.1M K-phosphate buffer solution; pH 8.8–10.0, $K_2CO_3$-$NaHCO_3$ buffer solution).

(2) Optimum temperature:
The optimum temperature of the present enzyme is in the vicinity of 35° to 40° C. under the aforementioned condition for the determination of enzymatic activity.

(3) pH and temperature stability:
When the present enzyme is treated for 15 minutes in a 0.1M dimethylglutaric acid-NaOH buffer solution (pH 7.0), it is stable up to 40° C., it keeps 30% of the activity even at 50° C., but it is completely inactivated at 55° C.

The present invention will be illustrated with reference to the following examples. Percents simply referred to in the examples are by weight.

EXAMPLE 1

To a basic culture medium containing 0.8% polypeptone, 0.6% yeast extract, 1.0% glycerol, 1.5% $K_2HPO_4$, 0.5% $KH_2PO_4$, 0.05% $MgSO_4.7H_2O$, 0.005% $FeSO_4.7H_2O$, 0.003% $MnCl_2.4H_2O$, 0.002% NaCl, 0.0002% $CaCl_2.2H_2O$ and 0.0001% $ZnSO_4.7H_2O$ was added 0.4% of each of α-GPO production promoting substances described in Table 1, and after adjusting the pH to 7.2, said each culture medium was added to 500-ml Sakaguchi flasks at a rate of 50 ml-flask and sterilized at 120° C. for 15 minutes. After cooling, the culture medium was inoculated by means of one platinum loop with microorganisms belonging to genus Pediococcus shown in Table 1, as previously stab-cultivated at 30° C. for 24 hours in a lactic acid bacteria stock culture medium (Nissui Sieyaku Co.), followed by shaking cultivation (135 s.p.m.) at 30° C. for 20 hours. After the cultivation, 5.0 ml of the culture broth was sampled from each flask, and centrifuged at 10,000 r.p.m. for 10 minutes to collect the cell. The cell obtained was re-suspended in 10 ml of a 0.1M K-phosphate buffer solution (pH 7.0) containing 0.005M EDTA and crushed by ultrasonic treatment to solubilize the enzyme. The crushed cell debris was removed by centrifugation, and the resulting supernatant liquor was analyzed for enzymatic activity. The activity of α-GPO is shown in Table 1. It was clearly recognized from Table 1 that the producibility of α-GPO is markedly increased by the addition of oxalacetic acid, α-ketobutyric acid, α-ketovaleric acid, α-ketogluconic acid or α-ketoglutaric acid.

TABLE 1

| | Influence of α-GPO production promoting substances on enzyme production | | | | | |
|---|---|---|---|---|---|---|
| | α-GPO production promoting substance Enzymatic activity (unit/ml of culture broth) | | | | | |
| Strain | None | Oxal-acetic acid | α-Keto-butyric acid | α-Keto-valeric acid | α-Keto-gluconic acid | α-Keto-glutaric acid |
| *Pediococcus acidilactici* (FERM BP-211) | 0.057 | 0.47 | 0.41 | 0.35 | 0.15 | 0.41 |
| *Pediococcus cerevisiae* (FERM BP-213) | 0.069 | 0.42 | 0.37 | 0.30 | 0.12 | 0.40 |
| *Pediococcus pentosaceus* (FERM BP-215) | 0.156 | 0.77 | 0.63 | 0.53 | 0.35 | 0.64 |
| *Pediococcus parvulus* (FERM BP-214) | 0.075 | 0.45 | 0.40 | 0.35 | 0.18 | 0.41 |
| *Pediococcus homari* (FERM BP-212) | 0.123 | 0.68 | 0.49 | 0.37 | 0.22 | 0.63 |
| *Pediococcus urinae-equi* | 0.040 | 0.35 | 0.32 | 0.32 | 0.15 | 0.38 |

TABLE 1-continued

| | Influence of α-GPO production promoting substances on enzyme production | | | | | |
|---|---|---|---|---|---|---|
| | | α-GPO production promoting substance Enzymatic activity (unit/ml of culture broth) | | | | |
| Strain | None | Oxal-acetic acid | α-Keto-butyric acid | α-Keto-valeric acid | α-Keto-gluconic acid | α-Keto-glutaric acid |
| IFO 12173 (ATCC 29722) | | | | | | |

EXAMPLE 2

To the basic or standard culture medium shown in Example 1 were added 0.4% of α-ketoglutaric acid and 0.04% of a defoaming agent, ADEKANOL LG-126 (produced by Asahi Denka Co.), and the pH was adjusted to 7.2. Fifteen liters of the nutrient medium thus obtained were added to a 30-liter fermenter and sterilized by steam at 121° C. for 15 minutes. The medium was then aseptically inoculated with 150 ml of a culture broth of *Pediococcus pentosaceus* (FERM BP-215) previously obtained by shaking cultivation at 30° C. for 15 hours in a 2-liter Sakaguchi flask using 350 ml of the nutrient medium of the same composition as above, followed by cultivation at 30° C. for 10 hours under aeration (14 liters/minute) and stirring (160 r.p.m.). After completion of the cultivation, 14 liters of the culture broth (8,400 unit) was treated by a continuous centrifugation to collect the cell. The harvested cell was suspended in 1 liter of a 0.05M K-phosphate buffer solution (pH 7.0).

This suspension was treated by a mill with glass beads to crush the cell. After crushing, the suspension was made up to 2 liters with a 0.05M K-phosphate buffer solution (pH 7.0), and the cell debris were removed by centrifugation. To the supernatant liquor obtained was first added ammonium sulfate to 40% saturation, and the insoluble matter was removed as precipitate by centrifugation. Thereafter, to the supernatant liquor obtained was further added ammonium sulfate to final 65% saturation to recover α-GPO as precipitate. Percent activity recovery as precipitate was 80%, and the specific activity was found to increase to about 8 times.

The precipitate obtained was dissolved in 200 ml of a 0.05M K-phosphate buffer solution (pH 7.0), and the resulting solution was desalted by passing through a column (1.5 liter capacity) packed with Sephadex G-25 (produced by Pharmacia Co.) and pre-equilibrated with a 0.05M K-phosphate buffer solution thereby to collect active fractions. The salt-free enzyme solution thus obtained was passed through a DEAE-Sepharose (produced by Pharmacia Co.) column (100 ml capacity) pre-equilibrated with a 0.05M K-phosphate buffer solution (pH 7.0) to adsorb α-GPO. After washing the column with the same buffer solution, the α-GPO was eluted with a stream of sodium chloride solution gradually increasing in concentration prepared by mixing 300 ml of the same buffer solution and 300 ml of the same buffer solution containing 0.5M sodium chloride so as to form the concentration gradient of sodium chloride. The eluted active fractions of α-GPO were combined, salted out with a 70% saturated ammonium sulfate to concentrate and then passed through a molecular sieve, Sephadex G-150 (produced by Pharmacia Co.) column, equilibrated with a 0.02M potassium phosphate buffer solution (pH 7.5). The finally obtained solution, GPO fractions passed through a molecular sieve, Sephadex G-150 column, was then lyophilized to obtain 73 mg of α-GPO preparation. The specific activity of this product was 34.2 U/mg, and the yield of the product from the extract was 37.2%.

EXAMPLE 3

Using as strain *Pediococcus acidilactici* FERM BP-211, *Pediococcus cerevisiae* FERM BP-213, Pediococcus parvulus FERM BP-214, *Pediococcus homari* FERM BP-212 and *Pediococcus urinae-equi* ATCC 29722, cultivation and purification were carried out in the same manner as in Example 2 to obtain lyophilized α-GPO having specific activity as shown below.

TABLE 2

| Strain | Specific activity (unit/mg) | Lyophilized product (mg) |
|---|---|---|
| *Pediococcus acidilactici* FERM BP-211 | 24.3 | 65 |
| *Pediococcus cerevisiae* FERM BP-213 | 22.1 | 72 |
| *Pediococcus parvulus* FERM BP-214 | 24.0 | 68 |
| *Pediococcus homari* FERM BP-212 | 32.0 | 71 |
| *Pediococcus urinae-equi* ATCC 29722 | 18.2 | 58 |

COMPARATIVE EXAMPLE 1

In the same manner as in Example 1, microorganisms belonging to genus Pediococcus shown in Table 3 were cultivated in a culture medium containing pyruvic acid, and the resulting α-GPO was collected. The activity of the α-GPO obtained as shown in Table 3.

TABLE 3

| Strain | α-GPO production promoting substance Enzymaric activity (unit/ml of culture broth) Pyruvic acid |
|---|---|
| *Pediococcus acidilactici* FERM BP-211 | 0.10 |
| *Pediococcus cerevisiae* FERM BP-213 | 0.11 |
| *Pediococcus pentosaceus* FERM BP-215 | 0.20 |
| *Pediococcus parvulus* FERM BP-214 | 0.15 |
| *Pediococcus homari* FERM BP-212 | 0.29 |
| *Pediococcus urinae-equi* ATCC 29722 | 0.10 |

EXAMPLE 4

The procedure of Example 1 was repeated except that a strain *Streptococcus faecium* IFO 12256 (ATCC 14432), *Lactobacillus leichmannii* IFO 3073 (ATCC 4797) or *Lactobacillus fermentum* IFO 3071 (ATCC 9338) was used. The results as shown in Table 4.

TABLE 4

| Strain | α-GPO production promoting substance Enzymatic activity (unit/ml of culture broth) | | | | | |
|---|---|---|---|---|---|---|
| | None | Oxal-acetic acid | α-Keto-butyric acid | α-Keto-valeric acid | α-Keto-gluconic acid | α-Keto-glutaric acid |
| *Streptococcus faecium* ATCC 14432 | 0.065 | 0.68 | 0.40 | 0.31 | 0.22 | 0.62 |
| *Lactobacillus leichmannii* ATCC 4797 | 0.003 | 0.10 | 0.07 | 0.05 | 0.04 | 0.08 |
| *Lactobacillus fermentum* ATCC 9338 | 0.002 | 0.08 | 0.06 | 0.05 | 0.03 | 0.07 |

EXAMPLE 5

The procedure of Example 2 was repeated except that a strain *Streptococcus faecium* IFO 12256 (ATCC 14432), *Lactobacillus leichmannii* IFO 3073 (ATCC 4797), or *Lactobacillus fermentum* IFO 3071 (ATCC 9338) was used to obtain α-GPO having specific activity as shown below.

TABLE 5

| Strain | Specific activity (unit/mg) | Lyophilized product (mg) |
|---|---|---|
| *Streptococcus faecium* ATCC 14432 | 30.5 | 68 |
| *Lactobacillus leichmannii* ATCC 4797 | 11.5 | 22 |
| *Lactobacillus fermentum* ATCC 9338 | 8.6 | 33 |

What is claimed is:

1. A method for producing α-glycerophosphate oxides characterized in that an α-glycerophosphate oxidase producing microorganism belonging to genus Pediococcus, Streptococcus, Lactobacillus or Leuconostoc is cultivated in a nutrient medium containing at least one compound selected from the group consisting of α-keto acids represented by the formula,

R—COCOOH wherein R is $CH_3(CH_2)_m-$, $HOOC(CH_2)_n-$ or $CH_2(OH)CH(OH)CH-(OH)CH-$ (in which m is an integer of 1 to 3 and n is an integer of 0 to 2) and salts thereof, and then α-glycerophosphate oxidase is recovered from the resulting culture broth.

2. A method as described in claim 1, wherein said α-keto acid is α-ketobutyric acid, α-ketovaleric acid, α-ketocaproic acid, α-ketomalonic acid, oxalacetic acid, α-ketoglutaric acid or α-ketogluconic acid.

3. A method as described in claim 1, wherein the salt of said acid is sodium salt, potassium salt or calcium salt.

4. A method as described in claim 1, wherein a compound selected from the α-keto acids and the salts thereof is added in an amount of 1 to 10 g/liter of culture medium.

5. A method as described in claim 1, wherein a compound selected from the α-keto acids and the salts thereof is added in an amount of 2 to 5 g/liter of culture medium.

6. A method as described in claim 1, wherein the microorganism is selected from the group consisting of *Pediococcus acidilactici* (FERM BP-211), *Pediococcus cerevisiae* (FERM BP-213), *Pediococcus pentosaceus* (FERM BP-215), *Pediococcus parvulus* (FERM BP-214), *Pediococcus homari* (FERM BP-212), *Pediococcus urinae-equi* (ATCC 29722), *Streptococcus faecalis* (IFO 3971), *Streptococcus faecium* (ATCC 14432), *Lactobacillus leichmannii* (ATCC 4797), *Lactobacillus fermentum* (ATCC 9338).

* * * * *